United States Patent [19]
Watanabe et al.

[11] Patent Number: 5,837,219
[45] Date of Patent: Nov. 17, 1998

[54] LABELLED ACYL-L-CARNITINE AND DIAGNOSTIC AGENT

[75] Inventors: Yasuyoshi Watanabe, Minoh; Hirohiko Kuratsune, Toyonaka; Teruo Kitani, Suita, all of Japan; Bengt Langström, Upsala, Sweden

[73] Assignee: Japan Science and Technology Corporation, Japan

[21] Appl. No.: 742,183

[22] Filed: Oct. 30, 1996

[30] Foreign Application Priority Data

Oct. 31, 1995 [JP] Japan .................................. 7-284002

[51] Int. Cl.$^6$ ........................... A61K 37/00; A61M 36/14
[52] U.S. Cl. ..................... 424/1.81; 424/1.11; 424/1.65
[58] Field of Search ................. 424/1.11, 1.37, 424/1.65, 1.81, 9.1, 9.3; 128/653.1, 653.2, 654

[56] References Cited

PUBLICATIONS

Davenport (1995), Nuclear Medicine and Biology, vol. 22, No. 6, pp. 699–709 "Propionyl–L–Carnitine: Labeling in the N–Methyl Position with Carbon–11 and Pharmacokinetic Studies in Rats."

Sherry et al (1985), J. Biological Chemistry, vol. 260, No. 16, pp. 9272–9279, "Metabolic Studies of Pyruvate–and Lactate–Perfused Guinea Pig Hearts by $^{13}$C NMR".

Sherry et al (1988), Biochem. J, vol. 254, pp. 593–598, "Propionate Metabolism in the Rat Heart by $^{13}$C n.m. r. Spectroscopy".

Anderson et al (1995), vol. 117, No. 42, pp. 10546–10550, J. Am. Chem. Soc. "Conformation of [Li–$^{13}$C, $^{15}$N] Acetyl–L–Carnitine. Rotational–Echo, Double–Resource Nuclear Magnetic Resonance Spectroscopy".

*Primary Examiner*—Gary E. Hollinden
*Assistant Examiner*—Dameron Jones
*Attorney, Agent, or Firm*—Wenderoth, Lind & Ponack, L.L.P.

[57] ABSTRACT

The present invention provides a labelled acyl-L-carnitine, which is an acyl-L-carnitine, a salt thereof or a derivative thereof, of which carbon group is labelled with a radionuclide or a stable isotope. It is possible to diagnose human diseases falling under acyl-carnitine metabolic syndrome, or human diseases due to structural/functional disorder of the brain by measuring the behavior of the labelled acyl-L-carnitine in various tissues or a biological sample from a subject administered with one or more kinds of the labelled acyl-L-carnitines.

8 Claims, 7 Drawing Sheets

LABELLED ACYL-L-CARNITINE AND DIAGNOSTIC AGENT

FIELD OF THE INVENTION

The present invention relates to a labelled acyl-L-carnitine and a diagnostic agent. More particularly, the present invention relates to a labelled acyl-L-carnitine useful as a diagnostic agent or the like which permits measurement of the behavior of acyl-carnitine contained in vivo or in a biological sample at a high sensitivity, and which makes it possible to easily and accurately inspect occurrence or the risk thereof of wasting diseases such as chronic fatigue syndrome, vascular disorder, diseases falling under acyl-carnitine metabolic deficient syndrome (ACMDS) such as stress diseases, cerebral diseases such as cerebral infarction, cerebral thrombosis and senile cerebral functional disorders.

DESCRIPTION OF THE RELATED ART

Carnitine is a physioactive substance which was first discovered in the muscle tissue in 1905, and it has so far been clarified that it plays an important role in uptake into mitochondria of long-chain fatty acid used as a major energy source for a body and adjustment of the short-chain fatty acyl CoA (coenzyme A)/CoA ratio in mitochondria.

Regarding acyl-carnitine (particularly acetyl-carnitine) formed by combination of carnitine with fatty acid, various studies have been made on pharmacological effects thereof with the use of experimental animals since about ten years ago. As a result, it is being clarified that administration of acyl-carnitine to a biological tissue or cells: a) has an effect on cerebral energy metabolism and adipose metabolism; b) extends the survival duration of neurons; c) prevents changes in structure of neurons with aging and inhibits decrease in learning efficiency; d) inhibits apoptosis of cells; and brings about many other pharmacological effects.

While acyl-carnitine is a physiological endogenous substance, the only fact reported to date in relation to changes of acyl-carnitine in vivo is that there is observed an increase in blood during fasting or exercise, and the present level of knowledge is far from clarification as to in what organ, tissue or cells in vivo acyl-carnitine is produced and how it functions.

Recently, the present inventors had doubt about the fact that patients of chronic fatigue syndrome (CFS) exhibited such muscular symptoms as muscular asthenia, myalgia or a strong feebleness after a light work, although no apparent abnormality was observed muscular-physiologically or in biochemical inspection in many of them. The present inventors therefore measured the value of carnitine and its derivatives in serum, and reported a peculiar phenomenon in which a CFS patient, while being normal in the value of free carnitine, showed an apparent decrease in acyl-carnitine combined with fatty acid (Clinical Infections Diseases 1994; 18 (Suppl. 1) S62-7). Thereafter, furthermore, the present inventors carried out studies using fasting/reintaking mice, and monkeys and persons before and after sugar tolerance and found the presence of a control mechanism centering around the liver, in which, in an energy crisis state, the liver produced acyl-carnitine, and when the necessity thereof decreased as a result of reintaking or sugar tolerance, acyl-carnitine is promptly incorporated from blood and stored in the liver.

With a view to measuring physiological, pharmacological or biochemical behavior of a trace substance in vivo, on the other hand, there are available various methods of administering in vivo a labelled substance to trace the behavior of the substance in a biological tissue or in a biological sample therefrom. Among others, commonly adopted methods include a method of synthesizing a positron-labelled compound with the use of a positron decay nucleus prepared in a cyclotron, administering it in vivo, and then measuring radioactivity in each tissue by positron emission tomography (PET); a method of administering in vivo a substance labelled with a stable isotope, and imaging nuclear magnetic resonance relative to electromagnetic wave irradiation in a highly magnetic environment (magnetic resonance imaging: MRI); and a method using a nuclear magnetic resonance spectroscopy (MRS). While these methods permit tracing the behavior of a labelled substance in various tissues of an individual, there is also available another method of using liquid chromatography, for example, for measuring a labelled substance in a biological sample such as urine or blood.

It is considered possible to diagnose symptoms and the risk of occurrence of human diseases falling under ACMDS by measuring the behavior of acyl-carnitine in a biological tissue or a biological sample as described above, but there has been unavailable a labelled compounds applicable for such diagnosis.

SUMMARY OF THE INVENTION

The present invention was developed on the basis of the relationship between acyl-carnitine metabolic abnormality and various diseases as found out by the present inventors, and has an object to provide a novel labelled substance which permits measurement of the behavior of acyl-carnitine in a biological tissue or a biological sample at a high sensitivity.

Another object of the present invention is to provide a diagnostic agent containing this labelled compound as an effective ingredient.

The present invention provides a labelled acyl-L-carnitine, which is an acyl-L-carnitine, a salt thereof or a derivative thereof, of which carbon group is labelled with radionuclide or stable isotope.

For the labelled acyl-L-carnitine of the present invention, a preferred embodiment is that the radionuclide is $^{11}C$ and the stable isotope is $^{13}C$.

Another preferred embodiment is that the labelled carbon group is a carbon atom forming carnitine group, primary carbon atom of acyl group, or carbon atom at any position from secondary to ω-terminal of acyl group.

Furthermore, the present invention provides a diagnostic agent used for diagnosing a human disease falling under acyl-carnitine metabolic syndrome, or a human disease due to a cerebral structural/functional disorder, which contains the foregoing labelled acyl-L-carnitine as an effective ingredient.

The labelled acyl-L-carnitine of the present invention makes it possible to diagnose various diseases caused by acyl-carnitine metabolic disorder or abnormal uptake thereof, or diseases due to cerebral structural or functional disorder by measuring the behavior of the labelled acyl-L-carnitine in urine or blood, and to determine localization of the labelled acyl-L-carnitine in a biological tissue through in vivo imaging by the PET method, MRI or MRS. It is now possible to obtain information about progress of therapeutic actions, thus permitting easy achievement of optimization of therapy.

DETAILED DESCRIPTION OF THE INVENTION

Acyl-L-carnitine in this labelled acyl-L-carnitine is a substance comprising a combination of carnitine and fatty acid, including acyl-L-carnitine, a salt thereof or a derivative thereof. Applicable acyl-L-carnitine compounds include carnitine having a normal-chain or branched-chain acyl group with carbon of about 2 to 26 such as acetyl-carnitine, propionyl-carnitine, butyryl-carnitine, isobutyryl-carnitine, valeryl-carnitine, isovaleryl-carnitine, pivaloyl-carnitine, hexanoyl-carnitine and lauroyl-carnitine. When using it in an inspection method described later or the like, an acyl-L-carnitine having carbon of 2 to 6 is preferable, and particularly, acetyl-carnitine and propionyl-carnitine are preferable.

The labelled acyl-L-carnitine as described above can be prepared, more specifically, by labelling carbon atoms forming carnitine group, primary carbon atom of acyl group, or carbon atom at any position from secondary to ω-terminal of acyl group with a radionuclide or a stable isotope by a known method. The labelled acyl-L-carnitine can be expressed by any of the following formulae (1) to (4):

[where, $R_1$ represents a direct bonding, or a normal-chain or branched-chain alkylene group or alkenylene group, and $^*C$ indicates a labelled carbon atom.]

[where, $R_1$ represents a direct bonding, or a normal-chain or branched-chain alkylene group or alkenylene group, and $^*C$ indicates a labelled carbon atom.]

[where, $R_1$ represents a direct bonding, or a normal-chain or branched-chain alkylene group or alkenylene group, and $^*C$ indicates a labelled carbon atom.]

[where, $R_2$ represents a direct bonding, or a normal-chain or branched-chain alkylene group or alkenylene group, and indicates that a carbon atom of any methylene group of the carbon chain is labelled.]

A $^{11}C$ may be used as the radionuclide label, and a $^{13}C$, as the stable isotope label.

The labelled acyl-L-carnitine of the present invention can be used furthermore for diagnosing various diseases due to acyl-carnitine metabolic abnormality or abnormal uptake of acyl-carnitine by measuring the behavior thereof in a biological sample such as urine or blood, or in a body with PET, MRI or MRS.

Human diseases of which symptoms or the risk of occurrence can be diagnosed by the use of the labelled acyl-L-carnitine of the invention are those symptoms and syndromes based on ACMDS, including symptoms relating to cell functional abnormality of the whole body such as general fatigue, headache, joint pain, slight fever, sleep disorder such as oversleep and insomnia, scotoma, photophobia, dark visual field, amnesia, hypersensitiveness, confusion, confusional thinking, absent-mindedness, perception disturbance, mobility disorder (paralysis and ataxia), psychoneurosis such as depression, anorexia, dryness such as eye-strain, digestive system disturbance (abdominal pain, neusea, diarrhea and constipation), xerostomia, night sweating, respiratory system disturbance (coughing, respiratory distress, short breath, pharynx pain, chest pain, etc.), circulatory organ disturbance (arrhythmia, tachycardia, bradycardia, violent palpitation, chest pain, shocked state, hypertension, hypotonia and other blood pressure abnormalities), frequent urination, oliguria, wet urination, leukocyte functional abnormality (decreased NK activity, lymphocytes functional abnormality, monocytes functional abnormality, etc.), and erythrocyte formal abnormality.

Furthermore, the labelled acyl-L-carnitine of the present invention is applicable also for diagnosis of human diseases due to cerebral structural and/or functional disorder. More specifically, the present inventors ligated the brain artery on one side of a monkey for making an ischemic model, and observed a very interesting fact that, in a brain portion on the blood flow decreasing side (ischemic side), uptake of acyl-carnitine as a ratio to the flow was unexpectedly accelerated. This suggests that, when sugar metabolism is prevented by a decrease in blood flow, for example, there is a mechanism of taking more acyl-carnitine up, and this mechanism contributes to brain metabolic compensation. It is possible at the same time to diagnose symptoms and syndromes of cerebral infarction, cerebral thrombosis, and senile cerebral functional disorders such as Alzheimer disease, by tracing the behavior of acyl-carnitine in the brain.

In addition, measurement of the behavior of the labelled acyl-L-carnitine in brain is applicable also for diagnosing various diseases based on the foregoing ACMDS. For the measurement of the behavior of acyl-carnitine in the brain, it is desirable to use an acyl-L-carnitine of which carbon atom at any position from secondary to ω-terminal of acyl group is labelled with $^{11}C$, because it is more efficiently taken up in the brain than any other labelled acyl-L-carnitine.

EXAMPLES

The present invention will be described below further in detail by means of examples. However, the present invention is not limited in any manner by the following examples.

The following compounds were previously prepared as intermediates of synthesis of the labelled acyl-L-carnitine in the following examples.

[$1-^{11}C$] Acetate (acetate with $^{11}C$-labelled primary carbon atom):

[$^{11}C$] Carbon dioxide was collected in a solution comprising 900 μl of dried diethylether, 200 μl of dried THF and 70 μl of 3M methyl magnesium bromide. After 30 seconds of reaction 1 ml of 1.2M HCl was added to evaporate diethylether in $N_2$ gas flow. The resultant crude product was purified by HPLC [Beckman Ultrasphere ODS C-18 10×250 mm, mobile phase: saline (0.9% NaCl)]. Analysis was carried out in a Beckman AX HPLC column (4.6×250 mm, 5 μm), mobile phase A: 0.01M $CaHPO_4$ (pH: 4.6) and B: MeOH, A/B=95/5.

[$2-^{11}C$] Acetate (acetate with $^{11}C$-labelled secondary carbon atom):

[$^{11}C$] Methyl iodide was synthesized by trapping [$^{11}C$] carbon dioxide in a THF 0.5 ml solution of 0.25M-hydrogenated aluminum-lithium. After evaporation of THF, 1 ml of 57% hydrogen iodide was added, and [$^{11}C$] methyl iodide was transferred into a solution of 500 μl of dried diethylether and 100 μl (160 μmol) of 1.6M n-butyllithium. After one minute of reaction, carbon dioxide gas was added (50 ml per minute, for 30 seconds). The reaction vessel was heated to 55° C. for two minutes to evaporate diethylether in $N_2$ gas flow. After adding 3 ml of 0.1M HCl and 1 ml of physiological saline, the resultant crude product was injected into HPLC column. The same HPLC system as for the [$1-^{11}C$] acetate synthesis was employed.

[$1-^{13}C$] Acetate (acetate with $^{13}C$-labelled primary carbon atom):

Synthesis was accomplished in the same manner as in the [$1-^{11}C$] acetate synthesis, except that 30 mg (280 μmol) of [$^{13}C$] $Na_2CO_3$ were dissolved in a space reactor into 2 ml of $H_2O$, and 1 ml of 1M HCl was added. The resultant [$^{13}C$] carbon dioxide was collected by means of a helium flow for reaction.

[$2-^{13}C$] Acetate (acetate with $^{13}C$-labelled secondary carbon atom):

Synthesis was accomplished in the same manner as in the [$2-^{11}C$] acetate synthesis, except that [$^{11}C$] methyl iodide was collected in n-butyllithium, and then 20 μl (64 μmol) of [$^{13}C$] methyl iodide was added. $H_2O$ was used as the mobile phase of thin-layer HPLC.

Example 1

Acetyl-L-carnitine with $^{11}C$-labelled primary carbon atom of acetyl group (ACN) was synthesized as follows.

An aqueous physiological saline solution (1.32 ml) of the above-mentioned [$1-^{11}C$] acetate was added to a solution of 400 μl of 0.5M Tris/HCl buffer (pH: 8.0), 20 μl (6 μmol) of 0.3M $MgCl_2$-$6H_2O$ 100 μl (10 μmol) of 0.1M ATP, 40 μl (2 μmol) of 50 mM coenzyme A (Sigma), 40 μl (400 μg, 3 units/mg protein) of acetyl-CoA synthetic enzyme (Boehringer Mannheim GmbH), 40μl (4 μmol) of 1.0M L-carnitine, and 40 μl (304 μg, 77 units/mg) of carnitine acetyl transferase (Sigma). The resultant solution was incubated at a temperature of 37° C. for five minutes, and 200 μl of 1.0M HCl were added to complete reaction. The reaction solution was passed through a filter of a fine pore diameter of 0.22 μm, and then poured into HPLC column (Beckman Ultrasphere ODS C-18 10×250 mm, mobile phase: 100% physiological saline).

Analysis was carried out in a Beckman CX HPLC column of 4.6×250 mm with mobile phase A: 0.01M $CaHPO_4$ (pH: 4.6) and B: MeOH=95/5.

Example 2

Acetyl-L-carnitine with $^{13}C$-labelled primary carbon atom of acetyl group was synthesized in the same manner as in Example 1, together with the following operations.

The foregoing [$1-^{13}C$] acetate ($H_2O$) in an amount of 1.4 ml was added to a solution of 800 μl of 0.5M Tris/HCl, 40 μl 1 (12 μmol) of 0.3M $MgCl_2$-$6H_2O$, 200 μl(20 μmol) of 0.1M ATP, 80 μl (8 μmol) of 100 mM coenzyme A, 80 ml (800 μg, 3 units/mg protein) of acetyl-CoA synthetic enzyme, 80 μl (8 μmol) of 0.1M L-carnitine, and 80 μl(608 μg, 77 units/mg) of carnitine acetyl transferase. The resultant solution was incubated at a temperature of 37° C. for 12 minutes, and purified by means of HPLC with $H_2O$ as the mobile phase.

The collected fraction was evaporated, dried and then diluted with $D_2O$. The $^{13}C$-NMR spectrum showed a δ 175.9 (reference: TSP) single peak, and it was confirmed that this peak corresponded to carbonyl group in acetyl group of O-acetyl-L-carnitine under the same conditions.

Example 3

Acetyl-L-carnitine with the $^{11}C$-labelled secondary carbon atom of acetyl group (ACM) was synthesized with the use of the foregoing [$2-^{11}C$] acetate in the same manner as in Example 1.

Example 4

Acetyl-L-carnitine with the $^{13}C$-labelled secondary carbon atom of acetyl group was synthesized with the use of the foregoing [$2-^{13}C$] acetate in the same manner as in Example 1. The $^{13}C$-NMR spectrum showed a δ23.8 (TSP) single peak, and it was confirmed that this peak corresponded to methyl carbon in O-acetyl-L-carnitine under the same conditions.

Example 5

L-carnitine with the $^{11}C$-labelled N-methyl carbon atom of carnitine (CRN) and acetyl-L-carnitine with the same label (ACC) were synthesized as follows.

By trapping [$^{11}C$] carbon dioxide in a THF 0.5 ml solution of hydrogenated 0.25M lithium-aluminum, [$^{11}C$] methyl iodide was synthesized. After evaporation of THF, 1 ml of 57% hydrogen iodide was added to transfer [$^{11}C$] methyl iodide into a solution (42 mg/350 μl $H_2O$) of 2 mg (13.5 μmol) desmethyl-L-carnitine, 200 μl DMSO and 50 μl (43 μmol) of $K_2CO_3$. The resultant solution was heated to a temperature of 90° C. for five minutes, and diluted with 2 ml $H_2O$ to adjust pH to 8 to 9. This solution was passed through an extraction column filled with 150 mg cation exchange resin (AG® 50 W-methyl, Bio-Rad Laboratories Richmond, Calif.) prepared with 2 ml ethanol and 2 ml $H_2O$ KOH (pH: 8.0). After rinsing with 2 ml $H_2O$ L-[$^{11}C$] carnitine was eluted by means of 0.5 ml 2M HCl into a 0.5 ml of 2M $Na_2CO_3$ solution. The resultant product was analyzed by HPLC using a Beckman CX column with A: 0.01 M CaHPO4 (pH: 4.6) and B: MeOH, A/B=95/5.

As a result of LC/MS analysis of a collected fraction, a value of m/z 162 corresponding to L-carnitine was obtained. The product was added to a solution of 400 μl of Tris/HCl buffer (pH: 8.0), 20 μl (2 μmol) of 0.1M acetyl-CoA and 20 μl (152 μg, 77 units/mg) of carnitine acetyl transferase. The solution was incubated at a temperature of 37° C. for five minutes.

The reaction was terminated by the addition of 200μl of 1.0M HCl. Then, the solution was passed through a filter of a fine pore diameter of 0.22 μm. The filtrate was purified and analyzed in the same HPLC system as in Example 1. LC/MS of the collected fraction showed a value of m/z 204 corresponding to acetyl-L-carnitine.

EXAMPLE 6

Acetyl-L-carnitine with $^{13}C$-labelled carnitine N-methyl carbon atom was synthesized in the same manner as in Example 5, together with the following additional operations. L-[N-methyl-$^{13}C$] Carnitine was added to a solution of 2 ml of 0.5M Tris/HCl buffer, 100 μl (10 μmol) of 0.1M acetyl-CoA, and 100 μl (760 μmol, 77 units/mg) of carnitine acetyl transferase, and the resultant solution was incubated for 15 minutes. $H_2O$ was used as the mobile phase of HPLC.

The collected fraction was evaporated and then diluted with $D_2O$. The $^{13}C$-NMR spectrum showed a δ57.2 single peak (TSP reference) corresponding to N-methyl carbon of O-acetyl-L-carnitine under the same conditions.

Example 7

Figure 1:
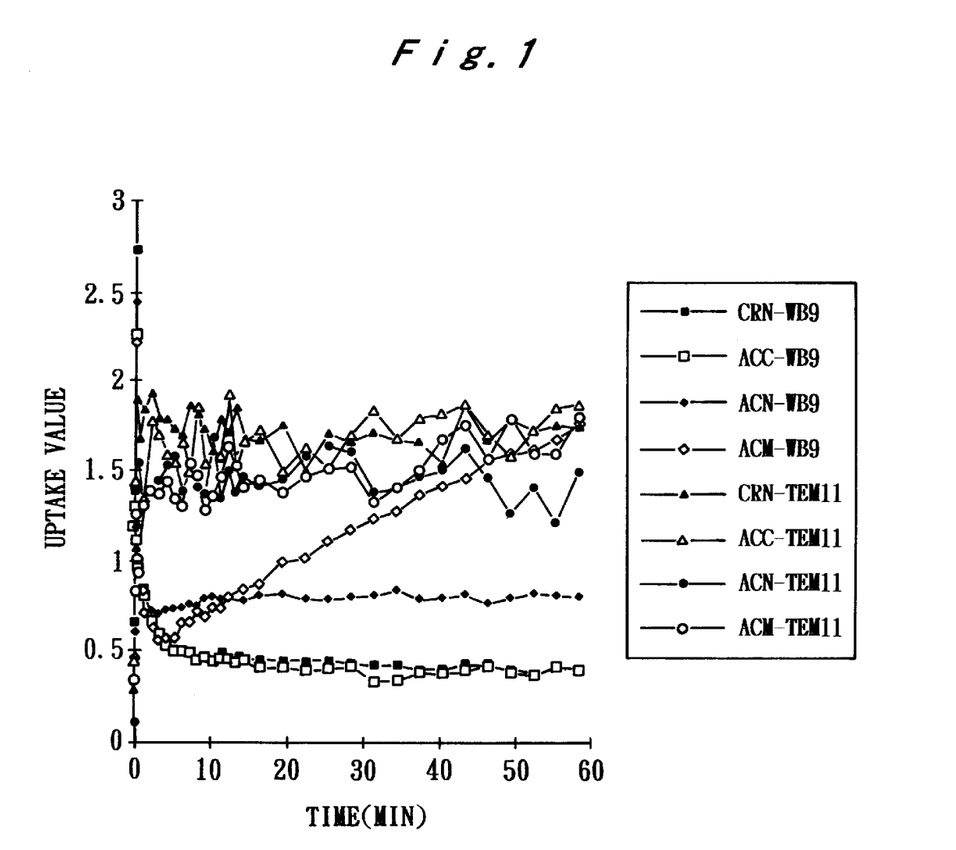
FIG. 1 is a graph illustrating changes with the passage of time in the uptake value of different position-labelled acetyl- L-carnitines (ACN, ACM and ACC) into the brain and temporal muscle of a rhesus monkey.

ACN, ACM, CRN and ACC prepared in Examples 1, 3 and 5 in equal amounts were intravenously administered to rhesus monkeys under anesthesia, respectively, at intervals of two hours, and the uptake value of those labelled compounds into the brain (whole brain: WB 9) and into the temporal muscle (TEM 11) was traced with time by the use of PET. The uptake value was obtained by the following calculation:

$$\frac{\left(\begin{array}{c}\text{radioactive counts in target tissue}\\\text{corrected value with decy}\\\text{and measuring efficiency}\end{array}\right)}{\text{total counts administered}} \div$$

$$\frac{\text{weight of the tissue}}{\text{body weight}} = \text{Uptake value of the labelled compound}$$

The results are as shown in FIG. 1: CRN and ACC with labelled carnitine carbon group were not taken up into the brain almost at all. ACN with a radiolabel in the primary carbon was taken up into the brain only slightly. In contrast, the brain uptake of ACM with a radiolabel in the secondary carbon atom was excellent: it was confirmed that the uptake of ACM into the brain was almost linearly increased up to 60 minutes after the administration.

In the uptake value into the temporal muscle, on the other hand, basically no difference was observed between labelling compounds.

It is confirmed from these results that, in order to measure the behavior of acyl-L-carnitine in the brain, it is effective to use an acyl-L-carnitine with at least the secondary carbon or carbon atom at a position from secondary to ω-terminal labelled as above.

Example 8

Figure 2:
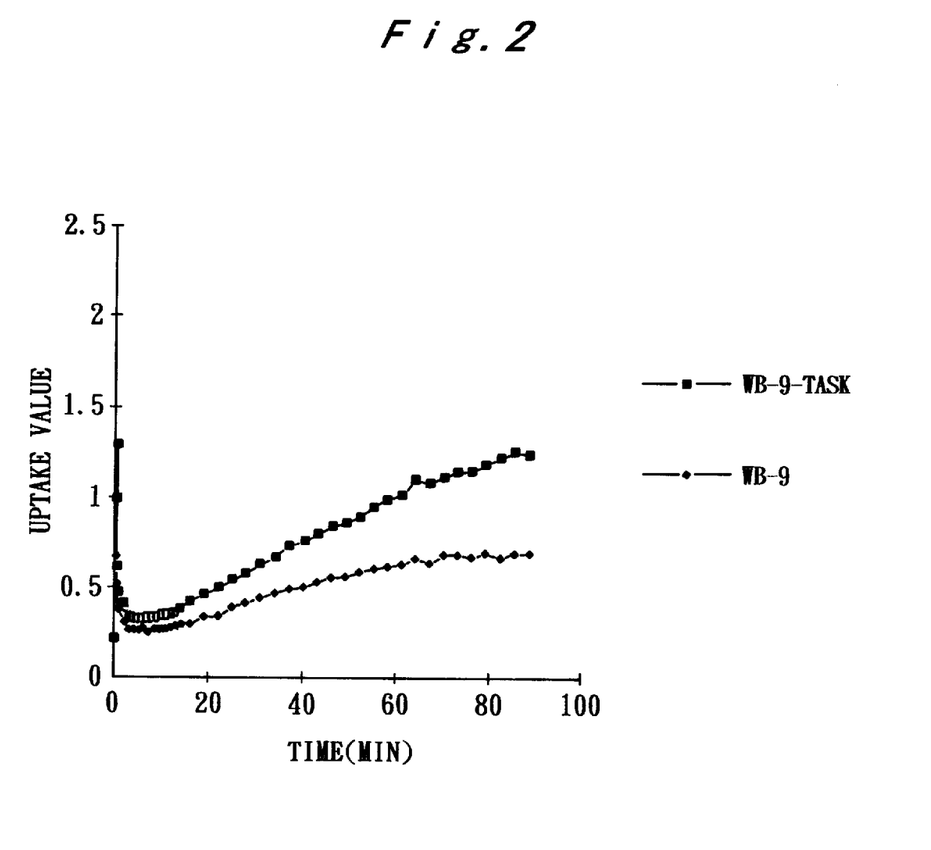
FIG. 2 is a graph illustrating changes with the passage of time in the uptake value of ACM into the whole brain of a healthy volunteer for each of the rest conditioon (WB 9) and task condition (WB 9-TASK).

ACM synthesized in Example 3 was intravenously administered to a normal volunteer, and the uptake value of ACM into the whole brain was measured by use of PET in both the rest condition (WR 9) and task condition (calculation task, memory task: WB9-TASK).

The results are shown in FIG. 2. It was confirmed again that ACM is taken up with time even during rest condition, and more importantly, it was proved that ACM is taken in the task condition in an amount about twice as large as that during rest.

These results suggest that there is a positive correlation between the brain function and the cerebral utilization usage of acyl-carnitine, and it is possible to accurately diagnose the presence of a structural and/or functional disorder of the brain or the extent thereof by measuring the behavior of labelled acyl-L-carnitine in the brain.

Example 9

Figure 3:
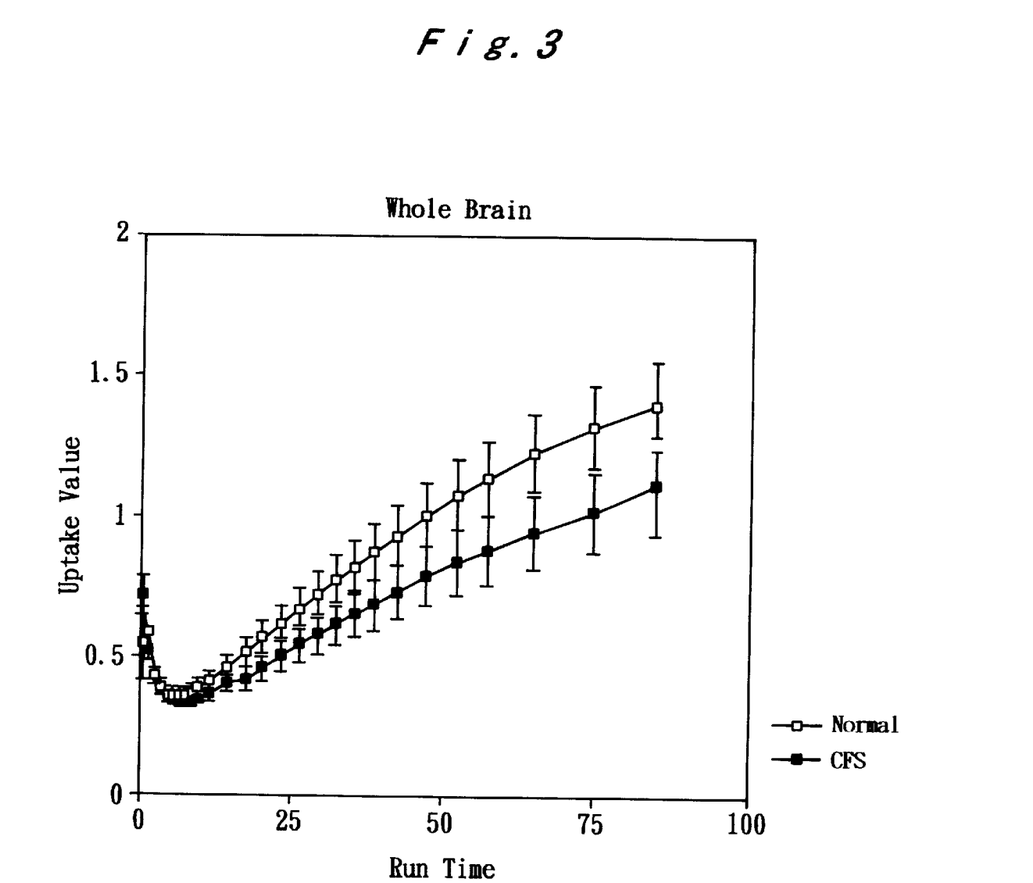
FIG. 3 is a graph illustrating changes with the passage of time in ACM uptake value into the whole brain of age-matched normal volunteers (n=5) and CFS patients (n=5).
Figure 4:
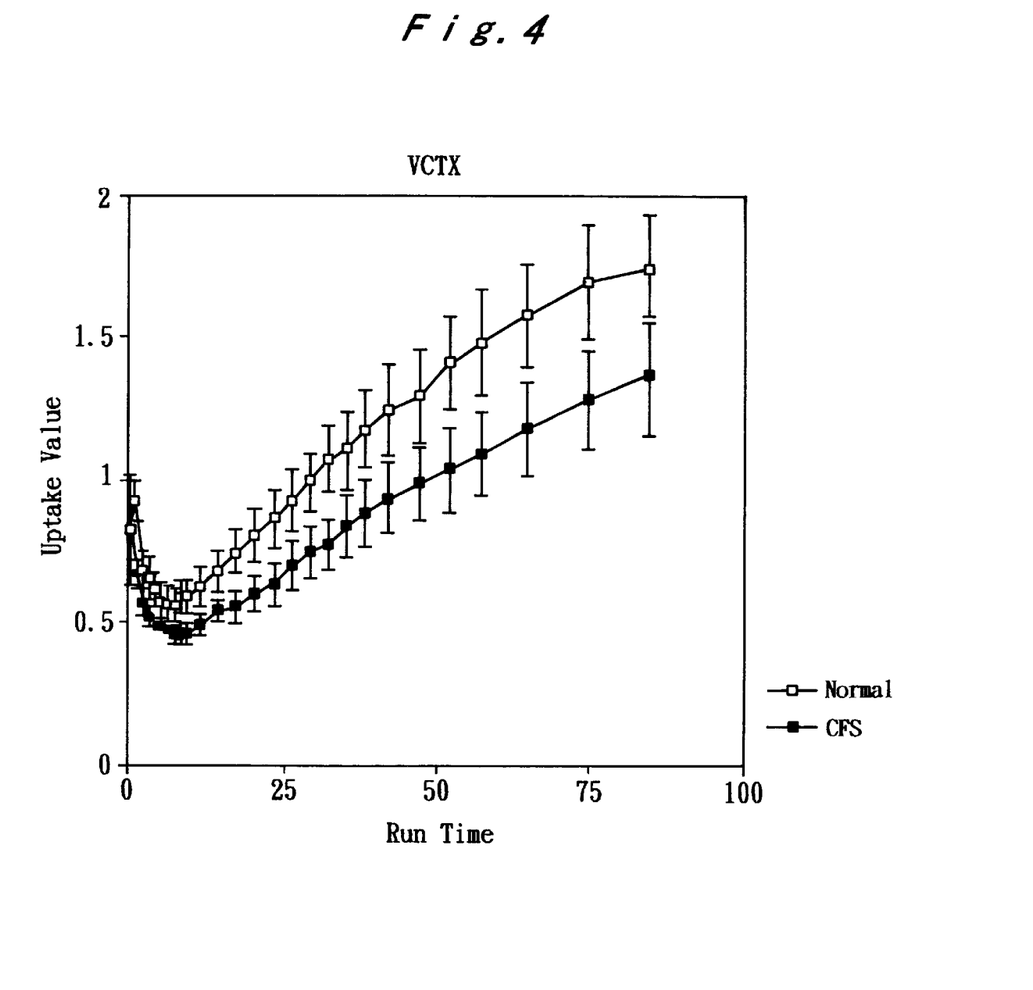
FIG. 4 is a graph illustrating changes with the passage of time in ACM uptake value into the visual cortex of normal volunteers (n=5) and CFS patients (n=6).

ACM synthesized in Example 1 was intravenously administered to normal volunteers (n=5) and CFS patients (n=6), and the ACM uptake values into the whole brain and visual cortex were measured with time by means of PET.

The results are shown in FIG. 3 (the result of whole brain) and FIG. 4 (of visual cortex): the increase with time in the ACM uptake value in the CFS patients was significantly lower than that in the normal volunteers, and the difference was particularly observed in the visual cortex than in the whole brain.

It was confirmed from these results that it was possible to diagnose the presence or the extent of a disease falling under CFS by administering the labelled acyl-L-carnitine (particularly ACM) to a person and measuring the behavior of ACM in the whole brain, or preferably, in the visual cortex of the brain.

Figure 5:
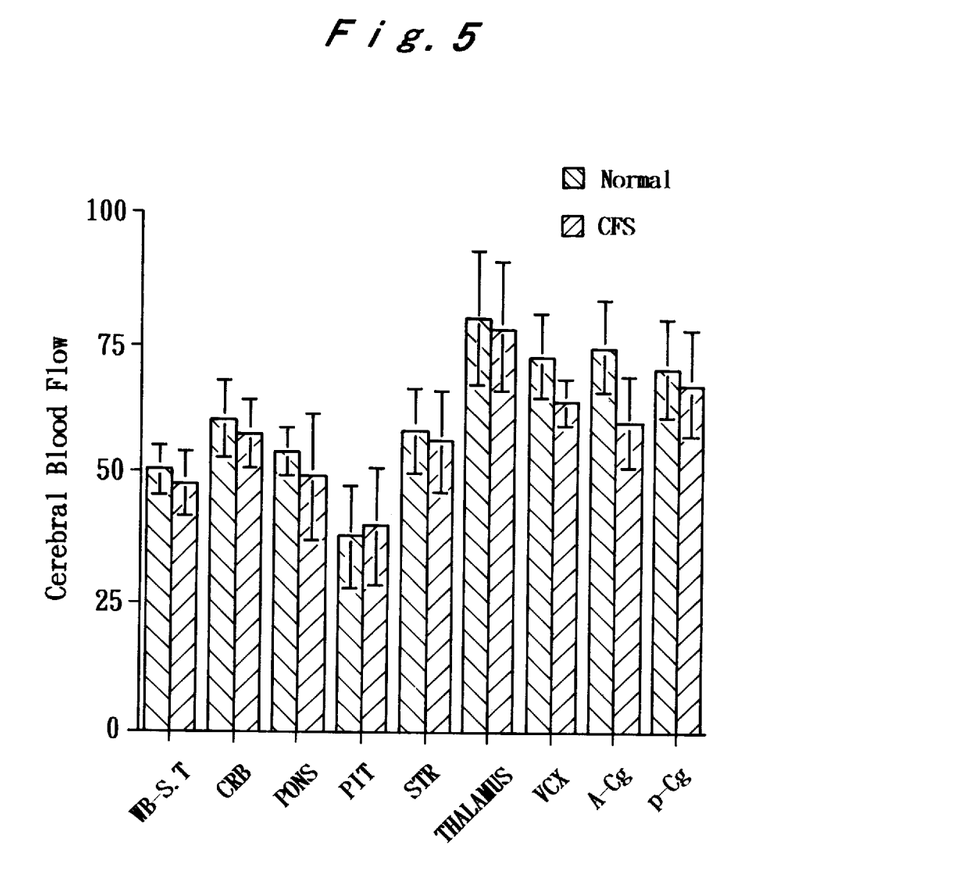
FIG. 5 is a graph illustrating the blood flow at various regions of the brain of normal volunteers (n=5) and CFS patients (n=6).

The decrease in the ACM uptake value in a CFS patient is not due to the decrease in the blood flow. More particularly, as shown in FIG. 5, the blood flow in various regions including the whole brain (WB-S.T.), visual cortex (VCX), cerebellum (CRB), pons (PONS), pituitary grand (PIT), corpus striatum (STR), thalamus (THALAMUS), anterior cingulate cortex (A-Cg), posteior cingulate cortex (PCg) was compared between the normal volunteers and CFS patients. No significant difference was observed between them, and this was also the case with the whole brain and the visual cortex for which significant differences were observed for the ACM uptake value.

Example 10

Figure 6:
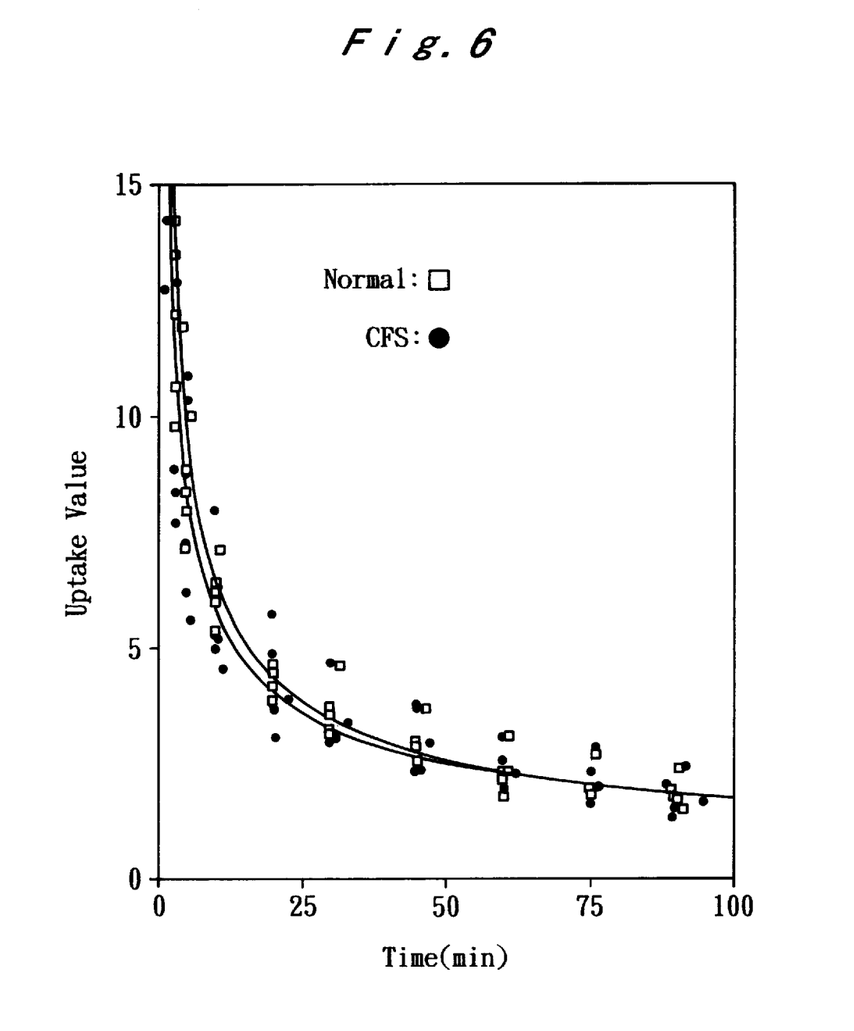
FIG. 6 is a graph illustrating changes with the passage of time in ACM uptake value into blood plasma of normal volunteers (n=5) and CFS patients (n=6).

Blood was sampled from the normal volunteers and the CFS patients and the ACM uptake values in the blood plasma and blood cells thereof was measured by the combined method of hematocrit tube and imaging plate.

The result is shown in FIG. 6: the ACM uptake value in blood plasma during almost the same course of lapse of time both for the normal volunteers and the CFS patients.

Figure 7:
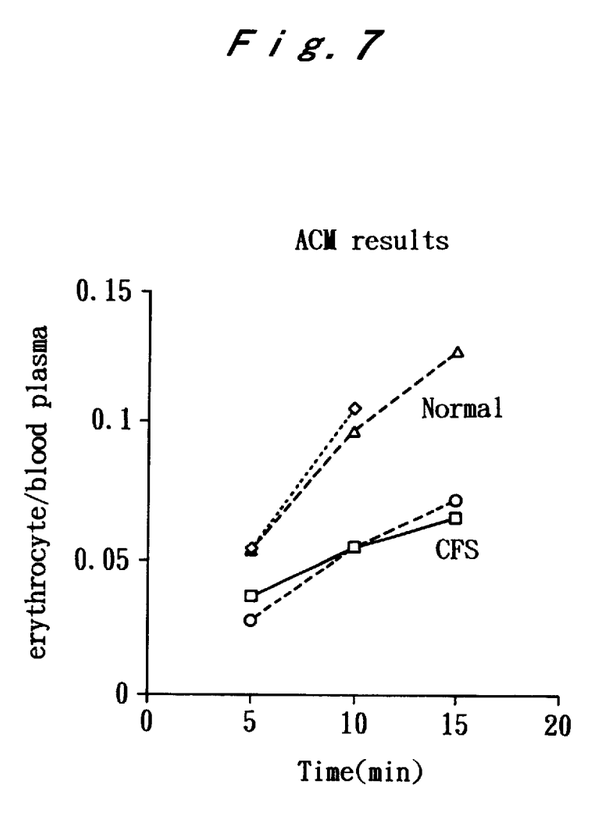
FIG. 7 is a graph illustrating changes with the passage of time in the ratio of ACM uptake value into erythrocytes and blood plasma of normal volunteers (n=2) and CFS patients (n=2).

However, while the ratio of erythrocyte to blood plasma (erythrocyte/blood plasma) as to the ACM uptake value increased with time in the normal subjects, this increase was inhibited in the CFS patients. This finding clearly suggests that the ACM uptake value into erythrocyte of the CFS patient is significantly lower than that in the normal volunteers, when considering that there is no difference in changes in the ACM uptake value into blood plasma between the normal volunteers and the CFS patients.

From the findings as described above, the possibility was confirmed to diagnose the presence or the extent of a disease falling under CFS also by measuring the behavior of the labelled acyl-L-carnitine of the present invention in blood.

What is claimed is:

1. A labelled acyl-L-carnitine, which is an acyl-L carnitine or a salt thereof, of which the secondary carbon atom of acyl group is labelled with $^{11}$C.

2. A labelled acyl-L-carnitine, which is an acyl-L-carnitine or a salt thereof, of which the secondary carbon atom of acyl group is labelled with $^{13}$C.

3. A diagnostic agent containing the labelled acyl-L-carnitine of claim 1.

4. A method for diagnosing the presence or the extent of a human disease due to an acyl-carnitine metabolic syndrome or a structural or functional disorder of the brain, which comprises administering to a human subject the diagnostic agent of claim 3 and then measuring uptake amount of the labelled acyl-L-carnitine in the whole brain or various brain regions after administration of said agent into said subject.

5. The method of claim 4, wherein the uptake amount of the labelled acyl-L-carnitine is measured by positron emission tomography, magnetic resonance spectroscopy, or magnetic resonance imaging.

6. A diagnostic agent containing the labelled acyl-L-carnitine of claim 2.

7. A method for diagnosing the presence or the extent of a human disease due to an acyl-carnitine metabolic syndrome, which comprises administering to a human subject the diagnostic agent of claim 6 and then measuring uptake amount of the labelled acyl-L-carnitine in a biological sample from said subject.

8. The method claimed in claim 7, wherein said biological sample is urine or blood from said subject.

* * * * *